United States Patent [19]

Schmidt et al.

[11] Patent Number: 4,772,743
[45] Date of Patent: Sep. 20, 1988

[54] BIFUNCTIONAL EMULSIFIERS BASED ON PERHYDROBISPHENOLS AND CARBOXYLIC ACID ANHYDRIDES

[75] Inventors: Adolf Schmidt, Cologne; Herbert Eichenauer, Dormagen; Alfred Pischtschan, Kuerten, all of Fed. Rep. of Germany

[73] Assignee: Bayer Aktiengesellschaft, Leverkusen, Fed. Rep. of Germany

[21] Appl. No.: 118,768

[22] Filed: Nov. 9, 1987

[30] Foreign Application Priority Data

Nov. 22, 1986 [DE] Fed. Rep. of Germany ....... 3639904

[51] Int. Cl.$^4$ ............... C07C 67/08; C07C 69/34; C07C 69/74; C07C 69/80
[52] U.S. Cl. ........................... 560/86; 560/98; 560/127; 560/194; 560/204
[58] Field of Search ............ 560/86, 98, 127, 194, 560/204

[56] References Cited

U.S. PATENT DOCUMENTS

| | | | |
|---|---|---|---|
| 4,199,517 | 4/1980 | Monte et al. | 560/86 X |
| 4,312,975 | 1/1982 | Salee et al. | 560/86 X |
| 4,618,699 | 10/1986 | Fialla. | |

*Primary Examiner*—Werren B. Lone
*Assistant Examiner*—Vera C. Clarke
*Attorney, Agent, or Firm*—Connolly and Hutz

[57] ABSTRACT

Reaction products of 1 mole 2,2-bis-(4-hydroxycyclohexyl)-propanes with 2 moles carboxylic acid anhydrides and their use as emulsifiers for emulsion polymerization.

2 Claims, No Drawings

BIFUNCTIONAL EMULSIFIERS BASED ON PERHYDROBISPHENOLS AND CARBOXYLIC ACID ANHYDRIDES

This invention relates to reaction products of 1 mole 2,2-bis-(4-hydroxycyclohexyl)-propanes corresponding to the following formula

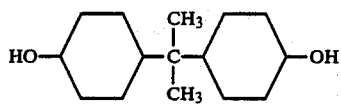   I with 2 moles carboxylic acid anhydrides corresponding to the following formula

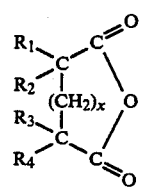   II in which, for x=0, $R_1$, $R_2$, $R_3$ and $R_4$ represent hydrogen or $R_1$ and/or $R_3$ represent $C_1$–$C_{35}$ alkyl or alkenyl and $R_2$ and $R_4$ and if appropriate $R_1$ or $R_3$ represent hydrogen or $R_1$ and $R_4$ together represent a chemical bond and $R_2$ and $R_3$ represent hydrogen or $R_1$ and $R_4$ together represent a chemical bond and $R_2$ and $R_3$ together with the carbon atoms represent an o-phenylene group or $R_1$ and $R_4$ together with the two CH groups (where $R_2$ and $R_3$=hydrogen) represent a two-valent cyclohexane, cyclohexane, norbornene or norbornane ring, for x=1, $R_1$, $R_2$, $R_3$ and $R_4$ represent hydrogen, which may be obtained by melting the components together at temperatures of from 100° to 300° C. in an inert gas atmosphere. These reaction products will also be called emulsifier resins.

The present invention also relates to a process wherein 2,2-bis-(4-hydroxyphenyl)-propanes corresponding to formula I and one or more carboxylic acid anhydrides corresponding to formula II are melted together in a molar ratio of 1:2 at a temperature of 100° to 300° C. and preferably at a temperature of from 120° to 220° C. in an inert gas atmosphere.

The present invention also relates to the use of the reaction products in the form of their alkali or ammonium salts as emulsifiers for emulsion polymerization.

Compounds corresponding to formula I are formed in the hydrogenation of bisphenol A. Mixtures of the trans-trans, the cis-trans and the cis-cis isomer can be formed (see U.S. Pat. No. 4,487,979). These compounds are commercial products (e.g. "perhydrobisphenol", manufactured by BAYER AG, which has a purity of at least 90%).

The following carboxylic acid anhydrides are suitable carboxylic acid anhydrides of formula II for the production of the emulsifier resins:

Succinic acid anhydride III, alkyl succinic acid anhydrides containing from 1 to 35 carbon atoms in the alkyl radical or alkylene radical IV and V, maleic acid anhydride VI, phthalic acid anhydride VII, tetrahydrophthalic acid anhydride VIII, hexahydrophthalic acid anhydride IX, 5-norbornene-2,3-dicarboxylic acid anhydride X, norbornane carboxylic acid anhydride XI, glutaric acid anhydride XII. The anhydrides correspond to the following formulae:

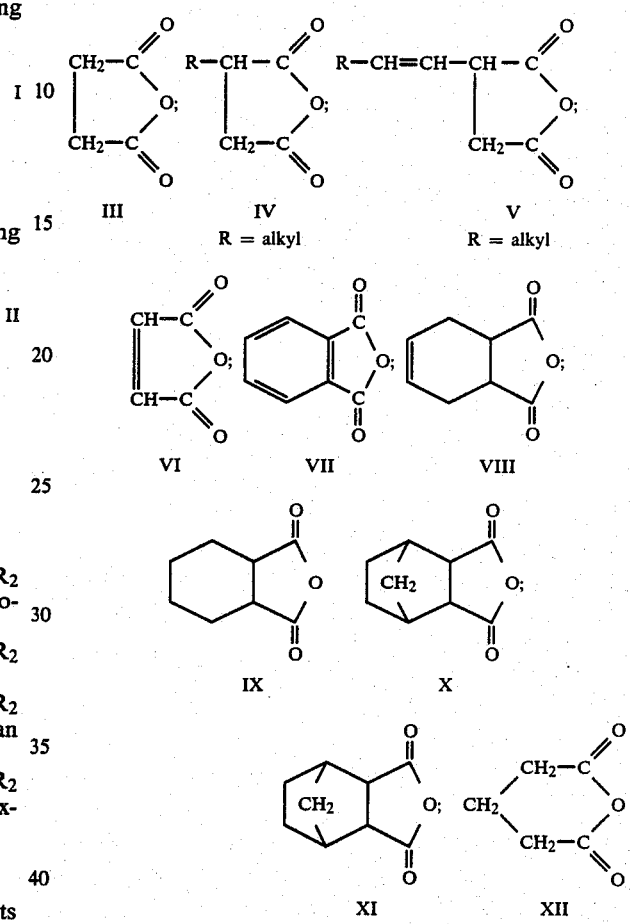

Preferred anhydrides yield after the reaction with the perhydrobisphenol acidic, light colored resins having softening points above 50° C. which can be powdered. Preferred emulsifier resins are obtained in the reaction of perhydrobisphenol with phthalic acid anhydride, tetrahydrophthalic acid anhydride, hexahydrophthalic acid anhydride, 5-norbornene-2,3-dicarboxylic acid anhydride, norbornane dicarboxylic acid anhydride (in a molar ratio of 1:2).

However, the preferred anhydrides mentioned can also be used in combination with the anhydride III to VI, preferably VI, by reacting 1 mole maleic acid anhydride and 1 mole of an anhydride III to V or VII to XII to 1 mole perhydrobisphenol.

Where 2 moles anhydride of formula IV or V are reacted with 1 mole perhydrobisphenol, the acidic resins are only readily soluble in aqueous alkali when the radical R contains no more than 18 carbon atoms. Where an anhydride of formula IV or V containing a very long-chain radical R (for example $R=C_{33}$-alkyl in formula V) is used, it is best to combine it with maleic acid anhydride, succinic acid anhydride or glutaric acid anhydride in a molar ratio of 1:1.

The reaction in the melt may be accelerated by catalysts, for example very small quantities of a tertiary amine, such as triethylamine, tributylamine, 1,4-diazabicyclo-octane. It is advisable to carry out the exothermic reaction with vigorous mixing. The end of the reaction may be determined by determining the acid number of the melt and is reflected in the disappearance of the anhydride band in the infrared spectrum. Nitrogen or argon may be used as the inert gas under which the reaction is carried out.

For the use as emulsifiers in accordance with the invention, the initially acidic, substantially water-insoluble resins are neutralized with alkali hydroxides, ammonia or amines. It is preferred to use aqueous potassium hydroxide because the potassium salts of the reaction products are particularly suitable as surfactants and emulsifiers by virtue of their good solubility in water.

The neutralization reaction of the acidic resins with aqueous alkali hydroxide can be monitored by conductometry. To this end, an exactly known amount, e.g., approximately 2 to 3 g of the resin is dissolved at room temperature in 100 ml pure isopropanol and the resulting solution titrated conductometrically with 1N potassium hydroxide.

The neutralized emulsifier resin solutions which show an alkaline reaction may be used with advantage as emulsifiers in the emulsion polymerization of radically polymerizable, ethylenically unsaturated monomers and of dienes, such as butadiene, isoprene, chloroprene, or in the copolymerization thereof.

There is a general need for heat-stable, substantially involatile emulsifiers which are highly compatible with the polymer and which lead to dispersions that are easy to coagulate, but can themselves be produced without any coagulate. The dispersions should not foam during removal of the residual monomers.

The emulsifier resins according to the invention very largely satisfy these requirements.

The dispersions prepared with the new emulsifiers may readily be coagulated by additions of mineral acids, organic acids, magnesium salts, calcium salts or sodium chloride, the poorly water-soluble emulsifier acids or their poorly soluble Ca or Mg salts remaining in the polymer. The coagulates may readily be washed out without any of the clouding observed with typical emulsifiers and without foaming in the water used to wash the coagulates.

The favorable emulsifier effect and the surfactant properties of the resin-like reaction products according to the invention were not foreseeable. They do not correspond to the conventional notion of an emulsifier as a molecule with a hydrophilic part and a long chain hydrophobic group (e.g. $C_{10}$–$C_{20}$-alkyl) attached thereto.

For example, surfactant properties cannot in any way be predicted for the reaction product of perhydrobisphenol and hexahydrophthalic acid anhydride or its alkali salt (XIII):

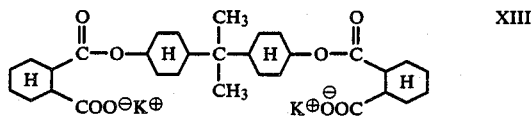

XIII

The structure of the dicarboxylic acid(s) shown in formula XIII was derived from the acid number and from molecular weight determination by the FAB (fast atom bombardment) method, negative measurement in triethanolamine. The significant peak is M/Z=547 (M-H)$^{\ominus}$ (Literature: M. Barber, R. S. Bordoli, R. D. Sedwik and A. N. Tyler, J. Chem. Soc. Chem. Commun. 325 (1981)).

It is not to be expected that compounds, such as the dipotassium salt XIII, are good micelle formers which enable the emulsion polymerization to be carried out on the lines of the generally developed notions (HARKINS). However, the following polymerization examples using monomers of relatively poor solubility in water (styrene and butadiene) demonstrate the surprising effectiveness of the emulsifier resins according to the invention.

An extensive series of polymerizations was carried out in the case of styrene to demonstrate the dependence of particle size on the quantity of emulsifier (cf. Examples 13–85 below).

In addition to the above-mentioned monomers, styrene and butadiene, the emulsifiers according to the invention can also be used for the polymerization of acrylates, methacrylates, for the copolymerization of acrylonitrile and/or methacrylonitrile with styrene, α-methyl styrene, acrylates and methacrylates. The copolymerization of butadiene and acrylonitrile is mentioned in particular.

The emulsifiers according to the invention can also be combined with other anionic or nonionic surfactants known per se. The polymerization reactions may be carried out by batch, monomer feed or continuous processes.

Some of the resins according to the invention, such as the reaction products with maleic acid anhydride or succinic acid anhydride with softening points below 40° C., show a tackiness reminiscent of that of natural resins. This tackiness may be entirely desirable in the processing of butadiene-styrene polymers for example.

The emulsifier resins according to the invention have improved color and constant emulsifying properties as compared to natural resins.

To remove residues of starting materials, for example perhydrobisphenol and, more particularly, anhydrides and water, the resins can be heated in a high vacuum and volatile fractions removed by distillation or sublimation.

EXAMPLES 1 to 12

Preparation of the emulsifier resins

The preparation of a number (1–12) of acidic emulsifier resins based on perhydrobisphenol (commercial product of BAYER AG) and various carboxylic acid anhydrides (cf. column 2) is described in Table I below.

The components were heated with stirring in the melt in the quantities indicated at the temperature shown in column 4 for the period shown in column 5, subsequently drained off in liquid form and optionally powdered. Column 7 shows the consumption in ml 1N KOH per gram acidic resin, as determined by conductometric titration, from which the acid number may be calculated (column 8, A.no. 1).

Finally, column 9 shows the calculated acid number of a reaction product where 1 mole perhydrobisphenol would have reacted with 2 moles anhydride to the α,ω-dicarboxylic acid. The two different acid numbers are referred to as A.no. 1 and A.no. 2. In most cases, the two acid numbers accord very well with one another.

EXAMPLES 13-84

Polymerization of styrene using the emulsifier resins

The acidic emulsifier resins obtained in accordance with Examples 1 to 12 are dissolved in the quantity of aqueous KOH necessary according to the determined acid number A.no. 1 and adjusted to a solids content of 5% by weight. Table IIa shows the increasing quantities of emulsifier (lines 3a to 3f) with which the particular emulsion polymerization of a certain quantity of styrene (114 g) was carried out for 7 hours at 70° C. in the absence of air in shaken bottles. After this period, the monomer conversion was substantially quantitative.

These 72 polymerization tests are evaluated according to particle diameter and quantity of coagulate in Table IIb below. The particle diameter was determined by turbidimetry and the values shown correspond to the diameter from the volume (DAV) (cf. DIN 53 206).

TABLE I

| Perhydro-bisphenol [g] | Reacted with | | [g] | Ex. resin no. | Reaction temperature [°C.] | Reaction time [mins.] | Softening point of resin [°C.] | Consumption ml 1N KOH/g substance | A.no. 1 | A.no. 2 |
|---|---|---|---|---|---|---|---|---|---|---|
| 120 | 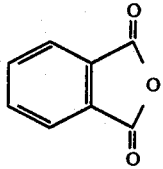 | phthalic acid anhydride | 148 | 1 | 210 | 15 | 180 | 3.76 | 211 | 209 |
| 180 | 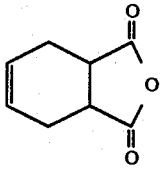 | tetrahydrophthalic acid anhydride | 228 | 2 | 130 | 180 | 3.91 | 219.4 | 206 | |
| 120 | 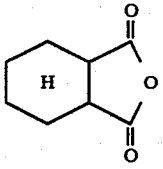 | hexahydrophthalic acid anhydride | 154 | 3 | 170 | 150 | 100 | 3.71 | 208.1 | 205 |
| 240 | 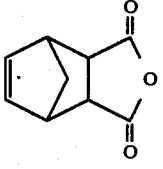 | 5-norbornene-2,3-carboxylic acid anhydride | 328.3 | 4 | 160 | 900 | 108 | 3.44 | 193.0 | 198 |
| 216 | 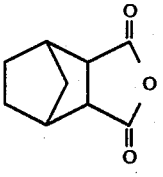 | norbornane-2,3-dicarboxylic acid | 299 | 5 | 140 | 1.300 | 96 | 3.65 | 204.8 | 196 |
| 180 | 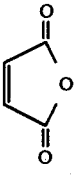 | malic acid anhydride | 147 | 6 | 125 | 240 | 35 | 4.70 | 263.7 | 257 |
| 180 | 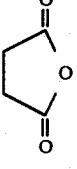 | succinic acid anhydride | 150 | 7 | 145 | 240 | 35 | 4.63 | 258.1 | 255 |

TABLE I-continued

| Perhydro-bisphenol [g] | Reacted with | | Ex. resin no. [g] | Reaction temperature [°C.] | Reaction time [mins.] | Softening point of resin [°C.] | Consumption ml 1N KOH/g substance | A.no. 1 | A.no. 2 |
|---|---|---|---|---|---|---|---|---|---|
| 180 | 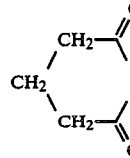 | glutaric acid anhydride | 171 8 | 130 | 240 | −8 | 4.46 | 250.2 | 240 |
| 120 | n-octylsuccinanhydride | | 212 9 | 115 | 115 | −5 | 3.54 | 198.6 | 169 |
| 90 | n-dodecylsuccinanhydride | | 243 10 | 115 | 115 | ±0 | 3.00 | 168.3 | 145 |
| 72 | n-octadecylsuccinanhydride | | 211 11 | 140 | 240 | 28 | 1.90 | 106.6 | 119 |
| 180 | maleic acid anhydride | | 73.5 | | | | | | |
| | hexahydrophthalic acid anhydride | | 118 12 | 125 | 240 | 72 | 4.24 | 237.9 | 238 |

TABLE IIa

| Polymerization temperature 70° C.; polymerization time 7 [h] | | | | | | |
|---|---|---|---|---|---|---|
| | a | b | c | d | e | f |
| Deionized water | 201.4 | 190.6 | 168.9 | 147.3 | 125.6 | 60.6 |
| Styrene | 114.0 | → | → | → | → | → |
| 5% emulsifier solution (K salts) | 11.4 | 22.8 | 45.6 | 68.4 | 91.2 | 159.6 |
| 1% K$_2$S$_2$O$_8$ solution | 34.2 | → | → | → | → | → |
| 1% Na$_2$CO$_3$ solution | 20.1 | → | → | → | → | → | emulsifiers produce minimal coagulate formation while the diameter of the latex particles is distinctly larger than the particle diameter obtained with standard emulsifiers. Accordingly, the polybutadiene latices shown are also thinly liquid and do not require larger additions of electrolyte.

Polybutadiene latices based on these emulsifiers may be grafted with styrene-acrylonitrile in known manner and processed to form ABS characterized by improved surface gloss and improved thermal stability.

TABLE IIb

| Example | Emulsifier of resin no..../ salt | Quantity of coagulate [g] for substantially complete conversion of the styrene | | | | | | Particle diameter (nm) | | | | | |
|---|---|---|---|---|---|---|---|---|---|---|---|---|---|
| | | a | b | c | d | e | f | a | b | c | d | e | f |
| 13–18 | ...1 | C* | 11 | 1.3 | 0.6 | 0.4 | 0.0 | — | 125 | 100 | 105 | 112 | 120 |
| 19–24 | 2 | C | 2 | 1.1 | 0.3 | 0.0 | 0.0 | — | 200 | 140 | 120 | 110 | 90 |
| 25–30 | 3 | C | 0.8 | 0.3 | 0.3 | 0.2 | 0.0 | — | 170 | 125 | 120 | 110 | 93 |
| 31–36 | 4 | C | C | 3.4 | 1.4 | 2.4 | K | — | — | 95 | 93 | 82 | 0 |
| 37–42 | 5 | C | C | 2.9 | 1.1 | 0.5 | 0.0 | — | — | 83 | 77 | 78 | 125 |
| 43–48 | 6 | C | C | 1.4 | 0.5 | 0.3 | 0.2 | — | — | 98 | 93 | 92 | 90 |
| 49–54 | 7 | C | C | 0.8 | 0.4 | 0.2 | 0.1 | — | — | 120 | 103 | 99 | 92 |
| 55–60 | 8 | C | C | 0.8 | 0.7 | 0.6 | 0.5 | — | — | 90 | 82 | 75 | 70 |
| 61–66 | 9 | C | C | 0.9 | 0.3 | 0.2 | 0.0 | — | — | 90 | 85 | 77 | 73 |
| 67–72 | 10 | C | 4.3 | 4.2 | 2.5 | 1.4 | 0.0 | — | 60 | 55 | 48 | 57 | 50 |
| 73–78 | 11 | C | 8.0 | 2.6 | 2.3 | 1.3 | 0.4 | — | 91 | 85 | 78 | 69 | 59 |
| 79–84 | 12 | C | C | 0.5 | 0.3 | 0.0 | 0.0 | — | — | 123 | 110 | 103 | 90 |

*C = Mixture completely coagulated

EXAMPLES 85–89

Polymerization of butadiene using the emulsifier resins

The following constituents are introduced in the absence of air into a 6-liter fine-steel autoclave with an infinitely variable paddle agitator (150 r.p.m.) and an electronically controllable internal temperature:

| | |
|---|---|
| Deionized water | 2282.00 g |
| Dipotassium salt* of the emulsifier acid, 100% WAS | 50.00 g |
| Tert.-dodecyl mercaptan | 5.00 g |
| 2.5% aqueous potassium peroxodisulfate solution | 155.00 g |
| Butadiene | 1650.00 g |

The contents of the autoclave are then heated to 65° C. and polymerized until the pressure falls (to a solids content of around 40% by weight).

In Table III, *"emulsifier" means the potassium salt of the resin shown in Table I, column 3.

Table III shows the polymerization results obtained where various dipotassium salts of emulsifier resins according to Table I, column 3, are used. The tested

TABLE III

| Polymerization of butadiene | | | | |
|---|---|---|---|---|
| Emulsifier* of resin no...., cf. Table I, col. 3, | Example | Precipitate (g) dry | Latex solids content % | Particle diameter DAV (nm) |
| 1 | 85 | 20 | approx. 40 | 80 |
| 3 | 86 | none | approx. 40 | 100 |
| 6 | 87 | 35 | 40 | 135 |
| 9 | 88 | 2.5 | 37 | 92 |
| 12 | 89 | none | approx. 40 | 112 |

The dispersions shown may be demonomerized without foaming and hence without difficulty. Demonomerization is not accompanied by the formation of coagulate.

EXAMPLE 92

Acrylonitrile-styrene is grafted onto the polybutadiene latex prepared in accordance with Example 86:

50 parts by weight polybutadiene (in the form of a latex having a solids content of 25% by weight), which has been prepared using

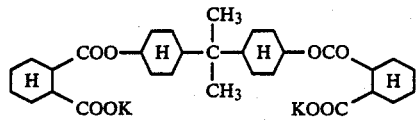

as emulsifier, are heated under nitrogen to 65° C., after which 0.5 part by weight potassium persulfate (dissolved in 15 parts by weight water) is added. A mixture of 36 parts by weight styrene and 14 parts by weight acrylonitrile and also 2 parts by weight of the sodium salt of disproportionated abietic acid (dissolved in 25 parts by weight water) are then added over a period of 4 hours, during which the grafting reaction takes place. Following an after-reaction, the latex is coagulated in a magnesium sulfate/acetic acid solution and the resulting powder is dried in vacuo at 70° C.

EXAMPLE 93

Testing of a mixture of the graft polymer described in Example 92 with a styrene/acrylonitrile copolymer 40 parts by weight of the graft polymer described in Example 92 were mixed with 60 parts by weight of a styrene/acrylonitrile resin (72:28, $M_w$ approx. 115,000; $M_w/M_n - 1 \leq 2$), 2 parts by weight of ethylenediamine bis-stearylamide and 0.1 part by weight of a silicone oil in an internal kneader and the resulting mixture injection molded to plates measuring 40×60×2 mm. The plates are assessed for natural color and surface gloss, the surface gloss being assessed on the A-H scale according to DE-AS No. 2 420 358.

| Processing temperature | Natural color | Gloss |
| --- | --- | --- |
| 240° C. | light | F |
| 260° C. | light | F |
| 280° C. | light | E-F |

EXAMPLE 94

Grafting of acrylonitrile/styrene onto the polybutadiene late prepared in accordance with Example 87

50 parts by weight polybutadiene (in the form of a latex having a solids content of 23% by weight), which has been prepared using

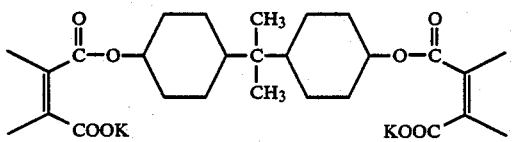

as emulsifier, were graftd as in Example 92 with 36 parts by weight styrene and 14 parts by weight acrylonitrile, worked up by coagulation and dried in vacuo at 70° C.

EXAMPLE 95

Testing of the graft polymer described in Example 94 after mixing with a styrene/acrylonitrile copolymer 40 parts by weight of the graft polymer described in Example 94 were mixed with 60 parts by weight of the styrene/acrylonitrile resin described in Example 93 and with the same additives and processed by injection molding.

Evaluation of the test plates produced the following results:

| Processing temperature | Natural color | Gloss |
| --- | --- | --- |
| 240° C. | light | F |
| 260° C. | light | F |
| 280° C. | light | E-F |

What is claimed is:
1. Reaction products of 1 mole 2,2-bis-(4-hydroxycyclohexyl)-propanes corresponding to the following formula

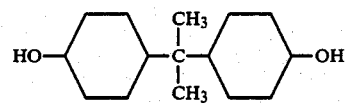

with 2 moles carboxylic acid anhydride corresponding to the following formula

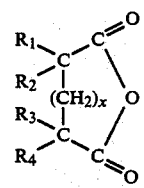

in which, for x=0,
$R_1$, $R_2$, $R_3$ and $R_4$ represent hydrogen or
$R_1$ and/or $R_3$ represent $C_1-C_{35}$ alkyl or alkenyl and $R_2$ and
$R_4$ and, if appropriate, $R_1$ or $R_3$ represent hydrogen or
$R_1$ and $R_4$ together represent a chemical bond and $R_2$ and $R_3$ represent hydrogen or
$R_1$ and $R_4$ together a chemical bond and $R_2$ and $R_3$ together with the carbon atom represent an o-phenylene group or
$R_1$ and $R_4$, together with the two CH groups (where $R_2$ and $R_2$ represent hydrogen), represent a 2-valent cyclohexene, cyclohexane, norbornene or norbornane ring,
for x=1,
$R_1$, $R_2$, $R_3$ and $R_4$ represent hydrogen,
obtainable by melting the components together in an inert gas atmosphere at temperatures of from 100° to 300° C.

2. A process for the preparation of the reaction products claimed in claim 1, wherein 2,2-bis-(4-hydroxyhexyl)-propanes corresponding to formula I and one or more carboxylic acid anhydrides corresponding to formula II are melted together in a molar ratio of 1:2 in an inert gas atmosphere and at a temperature of 100° to 300° C.

* * * * *